United States Patent
Yasseri et al.

(10) Patent No.: US 7,638,431 B2
(45) Date of Patent: Dec. 29, 2009

(54) COMPOSITE NANOSTRUCTURE APPARATUS AND METHOD

(75) Inventors: Amir A. Yasseri, Mountain View, CA (US); Theodore I. Kamins, Palo Alto, CA (US); Shashank Sharma, San Jose, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 288 days.

(21) Appl. No.: 11/537,589

(22) Filed: Sep. 29, 2006

(65) Prior Publication Data

US 2008/0081388 A1 Apr. 3, 2008

(51) Int. Cl.
*H01L 21/44* (2006.01)

(52) U.S. Cl. .............. 438/678; 257/E21.171; 257/E21.175; 977/857

(58) Field of Classification Search .......... 438/678; 257/E21.171, E21.175
See application file for complete search history.

(56) References Cited

U.S. PATENT DOCUMENTS

| | | | |
|---|---|---|---|
| 6,831,017 B1 * | 12/2004 | Li et al. ............. | 438/694 |
| 7,265,037 B2 | 9/2007 | Yang et al. | |
| 7,446,024 B2 * | 11/2008 | Kamins ............. | 438/478 |
| 2002/0065242 A1 * | 5/2002 | Ford et al. ............ | 514/44 |
| 2004/0018416 A1 * | 1/2004 | Choi et al. ............ | 429/44 |
| 2005/0133476 A1 | 6/2005 | Islam et al. | |
| 2006/0006463 A1 | 1/2006 | Islam et al. | |
| 2006/0057360 A1 * | 3/2006 | Samuelson et al. ...... | 428/323 |
| 2006/0097389 A1 | 5/2006 | Islam et al. | |
| 2006/0141268 A1 * | 6/2006 | Kalkan et al. ......... | 428/446 |
| 2006/0207647 A1 | 9/2006 | Tsakalakos et al. | |
| 2006/0225162 A1 * | 10/2006 | Yi ................. | 977/754 |
| 2007/0224104 A1 * | 9/2007 | Kim ............... | 423/445 B |

OTHER PUBLICATIONS

L. A. Porter, H. C. Choi, J. M. Schmeltzer, A. E. Ribbe, L. C. C. Elliott, and J. M. Buriak, Nano Lett. 2, 1369 (2002).*
Lon A. Porter et al., Controlled Electroless Deposition of Noble Metal Nanoparticle Films on Germanium Surfaces, Nano Letters, 2002, pp. 1067-1071, vol. 2, No. 10.
Boon K. Teo, Doing Chemistry on Low-Dimensional Silicon Surfaces: Silicon Nanowires as Platforms and Templates, Coordination Chemistry Review, 2003, pp. 229-246, 246.
X. H. Sun et al., Zero-Dimensional Nanodots on One-Dimensional Nanowires: Reductive Deposition of Metal Nanoparticles on Silicon Nanowires, Jun. 2004, pp. 199-224, vol. 15, No. 2.
A. A. Yasseri et al., Growth and Use of Metal Nanocrystal Assemblies on High-Density Silicon Nanowires Formed by Chemical Vapor Deposition, Appl. Phys. A—Materials Science & Processing, (2006) pp. 659-664, 82.

* cited by examiner

*Primary Examiner*—Michelle Estrada
*Assistant Examiner*—Jarrett J Stark

(57) ABSTRACT

A metal is deposited onto a surface electrochemically using a deposition solution including a metal salt. In making a composite nanostructure, the solution further includes an enhancer that promotes electrochemical deposition of the metal on the nanostructure. In a method of forming catalyzing nanoparticles, the metal preferentially deposits on a selected location of a surface that is exposed through a mask layer instead of on unexposed surfaces. A composite nanostructure apparatus includes an array of nanowires and the metal deposited on at least some nanowire surfaces. Some of the nanowires are heterogeneous, branched and include different adjacent axial segments with controlled axial lengths. In some deposition solutions, the enhancer one or both of controls oxide formation on the surface and causes metal nanocrystal formation. The deposition solution further includes a solvent that carries the metal salt and the enhancer.

20 Claims, 4 Drawing Sheets

COMPOSITE NANOSTRUCTURE APPARATUS AND METHOD

STATEMENT REGARDING FEDERALLY SPONSORED RESEARCH OR DEVELOPMENT

N/A

BACKGROUND

1. Technical Field

The invention relates to nanotechnology. In particular, the invention relates to nanostructures fabricated using electrochemical deposition techniques and to sensors using the nanostructures.

2. Description of Related Art

A consistent trend in semiconductor technology since its inception is toward smaller and smaller device dimensions and higher and higher device densities. As a result, an area of semiconductor technology that recently has seen explosive growth and generated considerable interest is nanotechnology. Nanotechnology is concerned with the fabrication and application of so-called nano-scale structures, structures having at least one linear dimension between 1 nm and 200 nm. These nano-scale structures are often 50 to 100 times smaller than conventional semiconductor structures and potentially can be fabricated less expensively by using 'bottom-up', self-assembly techniques.

Nanowires are building blocks of many potential nano-scale devices, such as nano-scale field effect transistors (FETs), p-n diodes, light emitting diodes (LEDs) and nanowire-based sensors, to name a few. There are many techniques known in the art for growing or forming nanowires. However, the area of nanotechnology needs ways to improve the robustness of nanowires for reproducible mass-fabrication of nano-scale devices in a manufacturing environment.

Accordingly, it would be desirable to have a nano-scale device providing robust nanowire-based enhanced sensing capability, and techniques to achieve the enhancements, which are conducive to a 'bottom-up' fabrication approach to the device. Such a nano-scale device and techniques would solve a long-standing need in the developing area of nanotechnology.

BRIEF SUMMARY

In some embodiments of the present invention, a method of making a composite nanostructure is provided. The method of making comprises enhancing a deposition solution that comprises a metal salt; and electrochemically depositing a metal from the enhanced deposition solution onto a nanostructure. Enhancing a deposition solution comprises introducing an enhancer to the deposition solution. The enhancer promotes electrochemical deposition of the metal onto the nanostructure.

In other embodiments of the present invention, a method of forming a catalyzing nanoparticle on a selected location of a surface from which a nanowire grows is provided. The method of forming comprises masking a surface, such that the selected location of the surface is exposed through a mask layer. The method of forming further comprises electrochemically depositing a metal nanoparticle on the surface in the selected location from a deposition solution of a metal salt. The metal nanoparticle preferentially deposits on the surface of the selected location instead of on unexposed surfaces.

In other embodiments of the present invention, a composite nanostructure apparatus is provided. The composite nanostructure apparatus comprises an array of nanowires on a substrate. Some of the nanowires are heterogeneous and branched. A heterogeneous branched nanowire comprises at least two adjacent axial segments that comprise different nanowire materials and a nanowire branch extending from at least one of the adjacent axial segments. The adjacent axial segments of at least one of the heterogeneous branched nanowires comprise controlled axial lengths. The composite nanostructure apparatus further comprises a metal deposited on at least some nanowire surfaces.

In other embodiments of the present invention, a deposition solution is provided. The deposition solution comprises a metal salt, means for enhancing electrochemical deposition of a metal from the metal salt in solution as a nanocrystal onto a surface; and a solvent. The metal salt and the means for enhancing are carried by the solvent. The means for enhancing one or both of controls oxide formation on the surface and causes metal nanocrystal formation.

Certain embodiments of the present invention have other features that are one or both of in addition to and in lieu of the features described hereinabove. These and other features of some embodiments of the invention are detailed below with reference to the following drawings.

BRIEF DESCRIPTION OF THE DRAWINGS

The various features of embodiments of the present invention may be more readily understood with reference to the following detailed description taken in conjunction with the accompanying drawings, where like reference numerals designate like structural elements, and in which.

DETAILED DESCRIPTION

Figure 1:
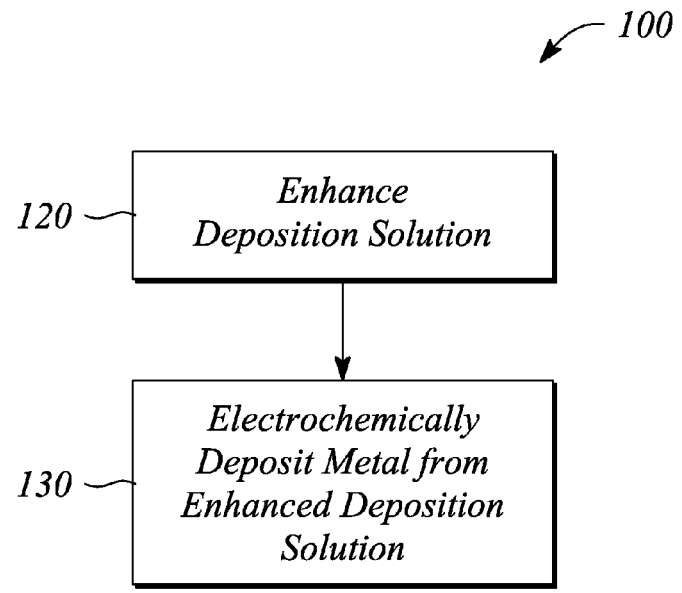
FIG. 1 illustrates a block diagram of a method of making a composite nanostructure according to an embodiment of the present invention.

Embodiments of the present invention employ electrochemical deposition to facilitate one or both of the fabrication and the use of nanostructures including composite nanostructures. As used herein, the term 'electrochemical deposition' is defined to include within its scope both 'electrodeposition' and 'electroless deposition', which are deposition techniques that are known in the art. In particular, the embodiments of the present invention electrochemically deposit nanocrystalline particles of a metal from solution onto a surface.

Herein, the term 'nanocrystalline particle(s)' of a metal is referred to interchangeably with 'nanocrystal(s)' or 'nanoparticle(s)' of the metal, 'the deposited metal', and 'the metal', unless otherwise indicated, for simplicity of discussion and not by way of limitation. In some embodiments, the nanostructure is a nanowire-based structure including, but not limited to, a nanowire and an array of nanowires. In these embodiments, reference to a 'surface' is a nanowire surface. The term 'nanostructure' is used interchangeably herein with 'nanowire' and 'nanowire array' for simplicity of discussion only and not by way of limitation. It should be understood that the term 'nanostructure' has broader meaning (e.g., nanotubes, nanoparticles) which is within the scope of the various embodiments of the present invention. In other embodiments, reference to a 'surface' is the surface of a substrate or a wafer from which a nanowire is grown or intended for growth. The term 'composite nanostructure' means a nanostructure comprising a metal deposited on a surface of the nanostructure.

Some embodiments of the present invention essentially control or limit growth of surface (native) oxides (i.e., oxidation of a surface) during electrochemical deposition of the metal from solution. These and other embodiments effectively one or more of increase the metal nuclei density on the surface, control the deposition process, and improve repeatability of the process relative to conventional electrochemical deposition. Some embodiments of the present invention facilitate molecular sensing using one or both of optical modes and electrochemical modes of detection including, but not limited to, Raman spectroscopy, surface enhanced Raman spectroscopy (SERS), voltammetry and amperometry, for example. Molecular sensing using composite nanowire-based structures as the sensing medium have improved or enhanced one or both of selectivity and sensitivity. In some embodiments, the present invention makes a nanostructure Raman-active for spectroscopic sensing and analysis purposes.

Moreover, some embodiments of the present invention facilitate controlling or selecting a location of catalyzing nanoparticles on a surface. Such embodiments may be used to select or control where nanowires grow on the respective surface, including primary growth nanowires and secondary growth nanowires (i.e., nanowire branches). Further, some embodiments of the present invention facilitate making composite branched nanowire structures that may be used in molecular sensing applications mentioned above. In some embodiments, the branched nanowire structures are formed with one or both of a controlled nanowire branch spacing and a selected nanowire branch location.

Electrodeposition comprises using a counter electrode, an external voltage source, and an electrodeposition bath that includes a metal ion in solution to be deposited as metal nanocrystals on the nanostructure surface. The nanostructure receives the metal nanocrystals from solution. The nanostructure may be an array of nanowires on a surface of a substrate, wherein the array comprises one or more nanowires. Moreover, the nanowire array that receives the metal nanocrystals comprises electrically conductive nanowires configured to afford good connectivity between nanowires in the array and the array substrate. The nanowire array effectively acts as a receiving electrode. Electrodeposition electrochemically deposits the metal nanocrystals on the surfaces of the electrically conductive nanowires using an applied voltage.

In electroless deposition, metal ions in solution electrochemically deposit as metal nanocrystals onto the surfaces of the nanowires in the array in a reduction-oxidation (redox) reaction without a need for a counter electrode, an applied voltage or a current resulting from the applied voltage. Moreover, the nanowires of the array may be electrically conductive, electrically nonconductive or semiconductive and may be either electrically connected or electrically isolated for electroless deposition. In some electroless deposition processes, an external reducing agent is introduced into the solution to facilitate the redox reaction (e.g., autocatalytic and substrate catalyzed processes). In other electroless deposition processes, no external reducing agent is used (e.g., surface-mediated or galvanic displacement process).

With respect to molecular sensing applications, the nanostructure or nanowire array having metal deposited on the nanowire surfaces (i.e., the composite nanostructure) exhibits enhancement in one or both of selectivity and sensitivity of the nanowires as a composite nanostructure sensor. For example, molecules to be sensed or detected (i.e., 'target molecule' or 'analyte molecule') will preferentially bind to, or otherwise preferentially interact with, the metal deposited on a nanowire surface, as opposed to an unmetalized nanowire surface, in molecular sensing applications. Moreover, the metal deposited on the nanowire surface facilitates fabricating complex composite nanowire structures. For example, a secondary nanowire will preferentially grow from a primary nanowire using a deposited metal nanoparticle as a catalyst to form a nanowire branch. Then, metal is further deposited on the nanowire branch or secondary nanowire, according to various embodiments of the present invention. In molecular sensing applications, such complex composite nanostructures have increased surface area for sensing. Therefore, composite nanostructures with increased sensitivity, for example, are realized in some embodiments of the present invention.

In an embodiment of the present invention, a method 100 of making a composite nanostructure is provided. The method 100 of making a composite nanostructure comprises electrochemically depositing a metal from a deposition solution to a nanostructure, such that the deposition of the metal on the nanostructure is promoted or enhanced. The deposition solution comprises a metal salt and an enhancer or means for enhancing the deposition. The electrochemical deposition of the metal is promoted or enhanced by the method 100 relative to an electrochemical deposition of the metal exclusive of the enhancer. Such enhancement is recognized or appreciated by one or more of an increase in metal nuclei density on the nanostructure surface, control of the deposition process, such that uniform nuclei density and size are achieved, and an improvement in process repeatability during the method 100 relative to using a metal salt solution exclusive of the enhancer. See published paper by A. A. Yasseri et al. "Growth and use of metal nanocrystal assemblies on high-density silicon nanowires formed by chemical vapor deposition", *Applied Physics A—Materials Science & Processing,* 82, 659-664 (2006), which is incorporated herein by reference.

In some embodiments, the metal deposits on the surface of the nanostructure as a result of a surface-mediated oxidation reduction (redox) reaction, which is also known as galvanic displacement, in the absence of an external or added reducing agent. In other embodiments, the metal deposits on the surface of the nanostructure in a redox reaction using a chemical reducing agent.

Typically during electrochemical deposition, the reduction and deposition of the metal compete with the oxidation of an essentially oxide-free surface and therefore, deposition of the metal is limited by the kinetics of the competing reactions. However, with the enhancer according to some embodiments of the present invention, the surface oxidation is controlled or limited, such that deposition of the metal as nanoparticles or nanocrystals on the nanowire array is enhanced. For example and not by way of limitation, in some embodiments, surface oxidation is controlled during deposition by replenishing a surface hydride species on a silicon nanostructure in a solution that comprises hydrogen fluoride (HF) as the enhancer. The HF solution removes (etches) oxidized silicon surface atoms ($SiO_2$) and hydrogen passivates newly exposed Si surface atoms. It is zero valence Si atoms on the surface of the nanostructure that then can reduce metal ions.

FIG. 1 illustrates a block diagram of the method 100 of making a composite nanostructure according to an embodiment of the present invention. Referring to FIG. 1, in some embodiments, the method 100 of making a composite nanostructure comprises enhancing 120 a deposition solution comprising a metal salt; and electrochemically depositing 130 a metal from the enhanced deposition solution on to a surface of the nanostructure. Enhancing 120 a deposition solution comprises introducing an enhancer to the deposition solution. The enhancer promotes electrochemical deposition of the metal from the enhanced deposition solution onto the nanostructure surface, such that a robust composite nanostructure is made or fabricated using the method 100. The deposition of metal on the nanostructure is promoted or enhanced by the enhancer, as described and defined herein.

In some embodiments, the method of making a composite nanostructure is a method of electrochemical deposition of a metal on a surface. During electrochemical 5 deposition of the metal, the introduced enhancer one or more of controls oxidation of the surface, removes oxide from the surface, reduces a metal ion of the metal salt to the corresponding metal, causes nanocrystal formation, and facilitates electrochemical formation of metal nanocrystals onto the surface, such that electrochemical deposition of the metal onto the surface is enhanced.

The metal salt comprises a salt of a transition metal. The transition metal includes, but is not limited to, one or more of gold (Au), silver (Ag), platinum (Pt), palladium (Pd), copper (Cu), nickel (Ni), iron (Fe), iridium (Ir), ruthenium (Ru) and rhodium (Rh), for example. The transition metals Au, Ag, Pt and Pd are also referred to herein as noble metals. Examples of a metal salt of gold and a metal salt of silver that are useful in some embodiments include, but are not limited to, $NaAuCl_4$ and $AgNO_3$, respectively. In some embodiments, the metal ion in solution of exemplary transition metals is Au(I)(III), Ag(I), Pt(I)(II), Pd(II, IV), Cu(II), Fe(II), Ir(IV), Ru(II), and Rh(III), for example and not by way of limitation. The transition metal deposits on the nanostructure as nanocrystalline particles (i.e., nanocrystals or nanoparticles).

As used herein, the term 'enhancer' or 'means for enhancing' is defined, for the purposes of the various embodiments of the present invention, to mean a chemical composition that one or both of provides control of (or limits) formation of oxide and causes nanocrystal formation on the nanostructure surface during electrochemical deposition, for example using either of the electroless deposition process or the electrodeposition process. As such, according to the definition herein, the enhancer or the means for enhancing facilitates and promotes one or more of an increase in metal nuclei density of the deposited metal on the surface, control of the deposition process to provide uniform nuclei density and size of the deposited metal nanocrystals, and an improvement in process repeatability, each relative to the respective electrochemical deposition using a metal salt solution without the enhancer.

In accordance with the definition of enhancer herein, providing control of formation of oxide (i.e., oxidation) on a surface includes within its scope, but is not limited to, one or more of limiting oxidation of the surface and removing oxide from the surface, depending on the embodiment. Moreover, causing nanocrystal formation includes within its scope, but is not limited to, one or more of reducing an ion of a metal salt to the corresponding metal nanocrystal, facilitating formation of metal nanocrystals on a surface and forming a hydrogen-terminated layer on the surface (e.g., of silicon) that, in turn, can reduce the metal ion, depending on the embodiment.

The enhancer includes, but is not limited to, one or more of a fluoride solution, an aldehyde, a carbohydrate, and hydrazine. In some embodiments, the enhancer is an oxide etchant that includes, but is not limited to, one or more of an aqueous solution of HF (i.e., water as a solvent), an aqueous solution of a buffered HF, and a nonaqueous fluoride solution (see examples of nonaqueous solvents below). A typical buffer for the aqueous solution of HF is ammonium fluoride, for example. In some embodiments, the enhancer is an organic chemical reducing agent including, but not limited to, an aldehyde, a carbohydrate, or hydrazine, each in a nonaqueous solvent. The enhancer promotes and facilitates the deposition of the metal from the solution on to the nanostructure surface. Using the enhancer, as defined above, the metal nanoparticles will preferentially deposit either by a surface mediated electrochemical reaction (i.e., galvanic displacement) or by an electrochemical reaction facilitated by the chemical reducing agent such that the nanoparticles form and subsequently preferentially deposit on the surface.

The deposition solution further comprises a solvent in which the metal salt and the enhancer are dissolved or carried. In an aqueous solution, water is the solvent. In a nonaqueous solution, the solvent is one or both of an anhydrous alcohol and a polar hydrocarbon including, but not limited to, one or more of methanol, ethanol, chloroform, tetrahydrofuran and dichloroethane, for example. In some embodiments, the solvent may facilitate the enhancer during deposition 130. For example, water alone is an effective oxide etchant for germanium oxide on germanium surfaces. Moreover, aqueous deposition solutions comprising water as the solvent and a fluoride solution as the enhancer promote or enhance the electrochemical deposition process for silicon, and possibly for germanium for example, by forming a hydride-terminated surface as described herein. However, aqueous deposition solutions comprising water as the solvent without an enhancer facilitate formation of native oxide on some nanowire materials, such as silicon. Therefore, water is included herein as the solvent for the aqueous deposition solutions of the present invention instead of being included herein as one of the enhancers, with the understanding that, in some embodiments, water further acts as an enhancer, as defined herein, in accordance with the invention.

In some embodiments, a nonaqueous deposition solution is used where the nanowire material is susceptible to oxidation in the presence of water. For example and not by way of limitation, some embodiments that use a silicon nanostructure for the method 100 of making a composite nanostructure employ a nonaqueous deposition solution. Such a nonaqueous deposition solution comprises the metal salt and the enhancer in one of the nonaqueous solvents listed herein.

During electrochemically depositing a metal 130, the metal will reductively deposit on the surface of the nanowires as one or both of a nanoparticle or nanocrystal of the metal and an accumulation of metal nanoparticles. The accumulation of metal nanoparticles includes within its scope a group or cluster of metal nanoparticles and a film or coating of metal nanoparticles on the nanowire surfaces. The film or coating may be either continuous or discontinuous including, but not limited to, a monolayer of metal nanoparticles. Hereinafter, the terms 'nanocrystals' and 'nanoparticles' will be used interchangeably to refer to the deposition of either a discrete nanoparticle of the metal or any of the above-described accumulations of the nanoparticles of the metal, unless otherwise indicated. Moreover, the term 'nanoparticle' includes the term 'nanoparticle catalyst' within its scope unless a distinction is provided.

The deposition of metal nanoparticles may depend on parameters of the enhanced deposition solution and of the electrochemical process. For example, parameters such as, but not limited to, reaction time and temperature and concentration of one or both of the metal salt and the enhancer, for example, may affect the metal deposition characteristics. In some embodiments, the concentration of metal salt in the solution ranges from about 1 mM to about 100 mM. In some embodiments, the concentration of the enhancer in the solution ranges from about 1% to about 49%. In some embodiments, the reaction time ranges from about 5 seconds to about 5 minutes; and the temperature ranges from about room temperature to about 80° C.). Such parameters are within the knowledge of one skilled in the art and do not require undue experimentation. For example, see an Example section, provided infra and the reference cited therein.

In some embodiments, an aliquot of the enhanced deposition solution is applied to the nanostructure (e.g., nanowires of the nanowire array). In other embodiments, the nanostructure (e.g., nanowires of the nanowire array) is immersed into the enhanced deposition solution.

Metal ions of the deposition solution in contact with the nanowire surfaces reductively deposit from the solution onto at least some of the nanowire surfaces. By 'reductively deposit' it is meant that the metal ions reduce to their solid metal counterpart and concomitantly deposit from solution as metal nanocrystals onto the nanowire surfaces. In embodiments that include a hydrogen-passivated surface on the nanowires, the surface itself effectively acts as a reducing agent in the presence of the metal ions in the deposition solution and facilitates the surface-mediated redox reaction, and hydrogen gas may evolve as a result of the redox reaction.

In some embodiments, the method 100 of making a composite nanostructure further comprises forming an array of nanowires as the nanostructure. In some embodiments, forming an array comprises growing the nanowires from a surface of a planar substrate. Techniques for growing nanowires are known in the art and include, but are not limited to, catalyzed growth, metal-catalyzed growth using vapor/liquid/solid (VLS) and metal-catalyzed growth using vapor/solid (hereinafter both are also referred to as 'CVD growth', for simplicity and not by way of limitation). In some embodiments, forming an array of nanowires comprises using one or both of a method 500 of forming catalyzing nanoparticles from which nanowires are grown, and a method 600 of forming a branched nanowire, both as described further below.

In some embodiments, the nanowires grow in a predominately perpendicular direction from a plane of the substrate surface. In other embodiments, the nanowires grow at an angle other than 90 degrees to the substrate surface. Nanowires will usually grow preferentially perpendicular to (111) planar surfaces of semiconductor substrates, for example. For additional information on forming nanowires, see co-pending U.S. Patent Application Publication Nos. US 2005-0133476 A1, published Jun. 23, 2005; and US 2006-0006463 A1, published Jan. 12, 2006; and co-pending U.S. patent application Ser. No. 10/982,051, filed Nov. 5, 2004; and Ser. No. 11/272,347, filed Nov. 10, 2005, all of which are incorporated herein by reference in their entirety.

In some embodiments, the method 100 of making a composite nanostructure further comprises removing oxide from the nanostructure, which according to the method 100, can be performed one or both of before and during electrochemically depositing 130 a metal, depending on the embodiment, as further described herein. In some of these embodiments, a native oxide is removed from nanowire surfaces of the array. In others of these embodiments, a non-native oxide is removed from nanowire surfaces of the array. As used herein, the term 'non-native oxide' refers to a grown or deposited oxide layer that is either relatively much thicker than an intrinsically formed 'native oxide' layer or of a higher quality than the native oxide layer. By 'higher quality' it is meant that the non-native oxide layer one or more of is denser, has higher permittivity, and has lower interface defect concentration compared to the native oxide layer. How each of the native oxide and the non-native oxide is removed depends on the material(s) of the nanowires.

For example, the oxide that forms on silicon nanowires is insoluble in water while the oxide that forms on germanium nanowires is soluble in water, as mentioned above. Therefore, removing oxide from nanowires that comprise silicon comprises exposing the silicon nanowire surfaces to an oxide etch solution, such as a solution comprising hydrogen fluoride (HF) or a buffered HF solution, for example, as is known in the art. In contrast, removing oxide from nanowires that comprise germanium typically comprises exposing the germanium nanowire surfaces to an oxide etch solution of water, since the oxide formed on germanium is water-soluble.

However, when the oxide is removed from silicon nanowires with the oxide etch solution comprising HF, a hydrogen-passivated layer is formed on the surface of the silicon nanowires, as described herein. The hydrogen-passivated layer comprises hydride-terminations on the silicon nanowire surfaces that facilitate electrochemically depositing 130 a metal, according to some embodiments of the method 100. While water removes the oxide from germanium, water typically does not (or is not known to) form hydride terminations on the germanium nanowire surfaces. A hydrogen passivated layer may be formed on the surface of germanium nanowires while removing oxide by using the oxide etch solution comprising HF, described herein for silicon. Moreover, heterogenous nanowires comprising axial segments of silicon and germanium, for example, may be treated with either an aqueous solution of HF or a nonaqueous fluoride solution, for example, to remove the oxides therefrom and to form a hydrogen passivated surface according to some embodiments of the method 100. However, a hydrogen passivated surface on the nanowires is optional for the purposes of the embodiments of the present invention.

In embodiments of the method 100 that include a fluoride solution to enhance 120 the deposition solution, removing oxide from the nanostructure effectively occurs at the same time a metal is being electrochemically deposited 130 on the nanostructure. Oxidation of the nanostructure is controlled or limited as well, such that the deposition of the metal is enhanced. In such embodiments, removing an oxide is performed simultaneously with electrochemically depositing 130 a metal as a single step. Moreover, in some embodiments, the hydrogen passivated surface of the nanostructure effectively acts as a 'surface reducing agent' in and of itself to facilitate the surface-mediated redox reaction (i.e., galvanic displacement) during electroless deposition 130.

Whether the electrochemical deposition of the metal nanocrystals is electroless or electrodeposition, the method 100 makes a robust composite nanostructure or composite nanostructure apparatus having more metal nanoparticles deposited on the nanostructure (i.e., enhanced deposition) relative to a composite nanostructure fabricated using an electrochemical deposition that does not include using the method 100, as described herein. The composite nanostructure apparatus of the present invention is useful for a variety of applications, including forming electrical contacts to the nanowires, growing branched nanowire structures, and sensing applications, as described further herein.

Figure 2:
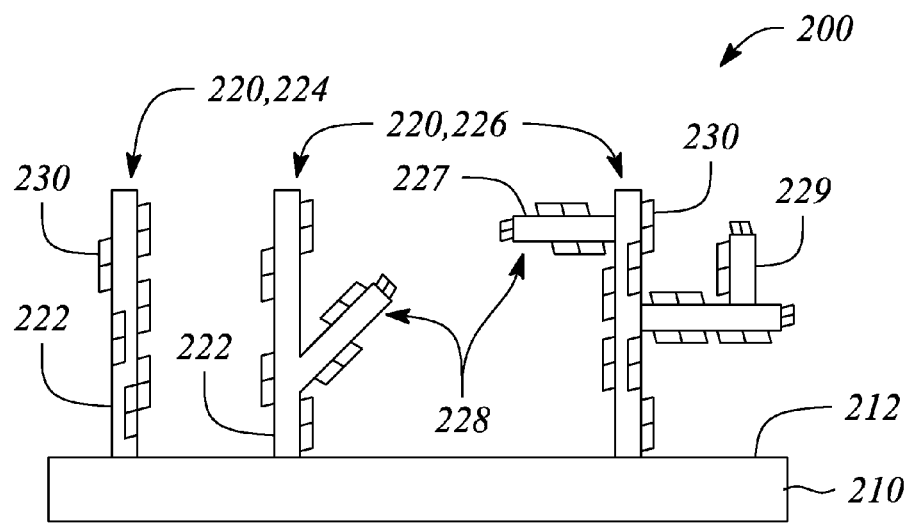
FIG. 2 illustrates a side view of a composite nanostructure apparatus according to various embodiments of the present invention.

FIG. 2 illustrates a side view of a composite nanostructure apparatus 200 according to various embodiments of the present invention. The composite nanostructure apparatus 200 comprises an array of nanowires 220 formed on a surface 212 of a substrate 210. In some embodiments, the composite nanostructure apparatus 200 comprises one or both of unbranched 224 nanowires and branched 226 nanowires. An unbranched nanowire 224 is a primary nanowire 224. The terms 'unbranched nanowire' and 'primary nanowire' may be used interchangeably herein without limiting the scope of the various embodiments. A branched nanowire 226 comprises a primary nanowire 224 and one or more secondary nanowires 228 or nanowire branches 228.

In the embodiment illustrated in FIG. 2, the primary nanowires 224 are grown in a predominately perpendicular direction from a plane of the substrate surface 212 for simplicity of illustration only. In fact, the primary nanowires 224 may be grown in a variety of angles from the substrate surface 212 and still be within the scope of the composite nanostructure apparatus 200 of the present invention. With respect to the branched nanowires 226, the secondary nanowires or branches 228 grow in a predominately perpendicular direction to a plane or surface 222 of the nanowire, although other directions have been observed and the scope of the embodiments herein are not intended to be limited to perpendicular secondary nanowire growth. FIG. 2 illustrates both a predominance of perpendicular secondary nanowires 228 and an exemplary nonperpendicular secondary nanowire 228 for that reason. Nanowire growth is described herein at least with respect to the method 100 of making a composite nanostructure. The formation of branched nanowires 226 is further described below with respect to a method 600 of forming branched nanowires.

The composite nanostructure apparatus 200 further comprises metal nanocrystals 230 deposited on some surfaces 222 of the nanowires 224, 226, and in some embodiments, on some surfaces 227 of the secondary nanowires 228. The metal nanocrystals 230 comprise one or both of a nanoparticle of the metal and accumulation of nanoparticles of the metal, as described above for the method 100 of making a composite nanostructure. The shapes and locations of the deposited metal nanocrystals 230 in FIG. 2 are illustrative only, not to scale, and not intended to limit the scope of the embodiments of the composite nanostructure apparatus 200. In some embodiments, the composite nanostructure apparatus 200 is fabricated according to the method 100 of making a composite nanostructure, described above. In some of these embodiments, the composite nanostructure apparatus 200 comprises one or both of increased nuclei density and uniform nuclei density and size of the deposited metal nanocrystals 230 relative to a composite nanostructure apparatus fabricated with a method other than the method 100 of the present invention.

A nanostructure, such as the nanowire 220, may be made from a material selected from one or more of a semiconductor, a metal and a nonmetal. For example, semiconductor materials include, but are not limited to, an elemental semiconductor of Group IV and various combinations of two or more elements from any of Groups III, IV, V and VI of the Periodic Table of the Elements. Moreover, any metal material including, but not limited to, aluminum (Al) and gallium (Ga); or any nonmetal material including, but not limited to, carbon (C), or combinations of metals and nonmetals, from the respective Groups of elements from the Periodic Table are useful as a nanowire material according to various embodiments of the present invention. For example and not by way of limitation, silicon (Si), germanium (Ge), silicon carbide (SiC), gallium arsenide (GaAs), gallium indium arsenide (GaInAs) and zinc oxide (ZnO), are a few non-limiting examples of the materials that are useful as a nanowire material according to some embodiments of the present invention. Also see the U.S. patent applications, cited supra, for materials used to make nanowires.

Figure 7:
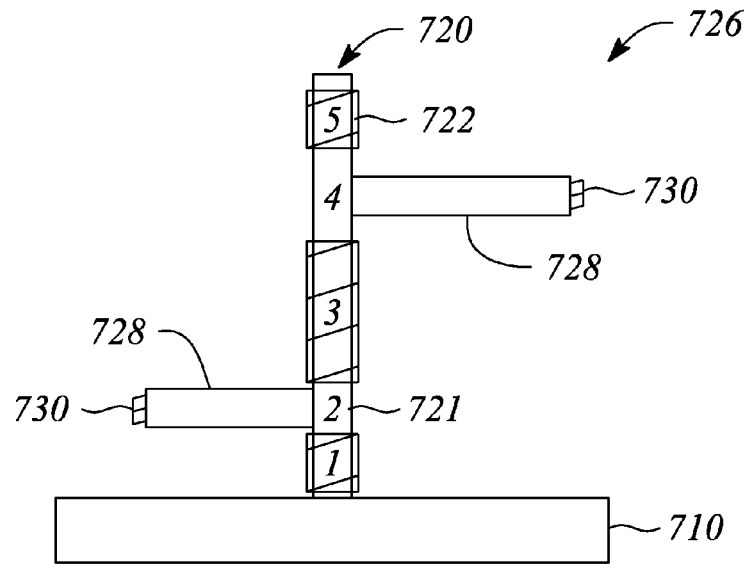
FIG. 7 illustrates a side view of a heterogeneous branched nanowire according to an embodiment of the present invention.

Moreover, a nanowire 220 of the array may be homogeneous or heterogeneous. A homogeneous nanowire comprises a single nanowire material for its entire axial length, excluding dopants. A heterogeneous nanowire includes at least two different axial nanowire segments along the axial length of the heterogeneous nanowire. By definition, a 'different nanowire segment' means that the axial segment comprises a different nanowire material from an adjacent nanowire segment. An exemplary heterogeneous nanowire may have two or three axial segments, for example: a first segment of a first nanowire material, a second segment of a second nanowire material that is different from the first semiconductor material, and optionally a third segment that is either a third and different nanowire material from the first and the second materials, or is the first nanowire material that alternates in axial segments with the second nanowire material along the axial length of the heterogeneous nanowire. An exemplary heterogeneous nanowire 720 is illustrated in FIG. 7 and described further below. For example and not by way of limitation, another exemplary heterogeneous nanowire may have a Si segment, followed by a Ge segment, that is followed by another Si segment or a segment of GaAs, (i.e., Si/Ge/Si heterogeneous nanowire or Si/Ge/GaAs heterogeneous nanowire, respectively).

Referring back to FIG. 2, both homogeneous and heterogeneous semiconductor nanowires 220 may be doped to provide specific characteristics to the nanowire including, but not limited to, a level of electrical conductivity to the nanowire. Dopant materials used in semiconductor technology are known in the art. For example, boron and phosphorous are typical doping materials used to modify the electrical conductivity of the base nanowire semiconductor material.

The substrate 210 is made of any of the above-mentioned materials, any combination of above-mentioned materials, or may be made from other materials not mentioned above, but within the knowledge of the skilled artisan, depending on the embodiment. Moreover, in some embodiments, the substrate 210 may include an insulating portion or an insulating layer to facilitate isolation between parts of the substrate. For example and not by way of limitation, the substrate may be a gallium arsenide wafer, a silicon wafer or a silicon-on-insulator (SOI) wafer. In some embodiments, the substrate 210 may include a conductive layer or region that electrically interconnects electrically conductive nanowires of the array for electrodeposition. In some embodiments, the substrate may be doped to impart electrical conductivity in portions or regions of the substrate. Moreover, a crystalline substrate may be cut or provided in a specified crystal lattice orientation. For example and not by way of limitation, semiconductor wafers having one of a [110] crystal orientation, a [100] crystal orientation and a [111] crystal orientation may be used according to various embodiments of the present invention. Further, the substrate may be processed to form an exposed surface plane of a desired orientation.

As mentioned above for the method 100 of making a composite nanostructure, the metal nanoparticles 230 deposited on the surfaces 222, 227 of the nanowires 220 of the composite nanostructure apparatus 200 comprise a transition metal selected from any of the metals listed above, for example. For the purposes of simplicity of discussion herein and not by way of limitation, examples herein may be described with reference to including one or more of a silicon substrate, a silicon-on-insulator substrate; silicon nanowires, germanium nanowires, or a heterogeneous combination thereof; and one or more of silver, gold and platinum as exemplary metal that is deposited. When any of these exemplary materials are referenced in a particular embodiment herein, one skilled in the art should recognize that other materials, whether described herein or otherwise known in the art, may be substituted for the exemplary material and still be within the scope of the present invention.

Figure 3:
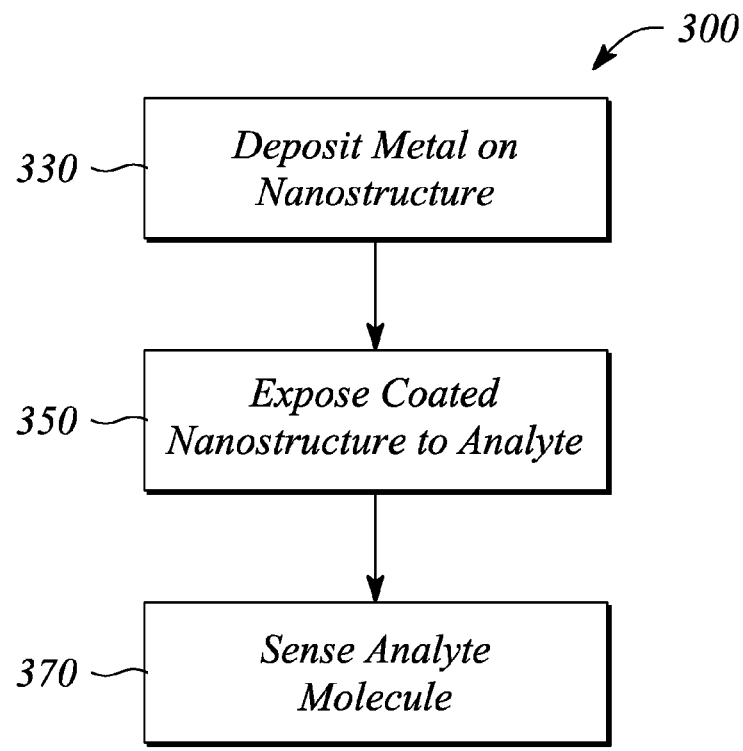
FIG. 3 illustrates a block diagram of a method of molecular sensing using a composite nanostructure according to an embodiment of the present invention.

In another embodiment of the present invention, a method 300 of molecular sensing using nanowires is provided. FIG. 3 illustrates a block diagram of the method 300 of molecular sensing according to an embodiment of the present invention. The method 300 of molecular sensing comprises depositing 330 metal nanoparticles on nanowire surfaces of an array of nanowires; exposing 350 the metal nanoparticles deposited 330 on the array to an analyte molecule; and sensing 370 an analyte molecule bound to the metal nanoparticles of the array.

Depositing 330 metal nanoparticles on nanowire surfaces of an array of nanowires uses electrochemical deposition to deposit 330 the metal nanoparticles on the nanowire surfaces, including one of electrodeposition and electroless deposition. The metal nanoparticles reductively deposit 330 from solution onto at least some of the nanowire surfaces. In some embodiments where the nanowire comprises silicon, for example and not by way of limitation, a hydrogen passivated layer is formed on the nanowire surfaces one or both of prior to and during depositing 330, such that the hydrogen terminated Si atoms on the nanowire surfaces effectively act as a reducing agent in the surface-mediated redox reaction with the metal ions during depositing 330.

In some embodiments, depositing 330 comprises introducing a deposition solution comprising a salt of a transition metal and an enhancer to the nanowire array. The enhancer facilitates the metal deposition 330. In some embodiments, the enhancer removes native oxide from the surfaces of nanowires of the array and controls or limits oxidation of the nanowire surfaces while the metal nanoparticles deposit 330 from the solution onto the nanowire surfaces in a surface-mediated redox reaction. In some embodiments, depositing 330 is essentially the same as that described above for the various embodiments of the method 100 of making a composite nanostructure. Moreover, in some embodiments, the nanowire array with metal nanoparticles deposited 330 on the nanowire surfaces is essentially the same as the composite nanostructure apparatus 200, also described above. Hereinafter, the nanowire array with the deposited metal nanoparticles that forms by depositing 330 will be referred to as the 'composite nanostructure apparatus', for simplicity of discussion and not by way of limitation.

Exposing 350 the metal nanoparticles of the method 300 of molecular sensing comprises exposing the composite nanostructure apparatus to a sample of the analyte molecule, such that the analyte molecule sample interacts or associates with the deposited 330 metal nanoparticles on the nanowires in preference to nanowires without the deposited metal nanoparticles. Effectively, the composite nanostructure apparatus according to the present invention is one or both of selective and sensitive to analyte molecules due to the preferential interaction and therefore, is a robust sensor apparatus, in some embodiments. Association of the metal nanoparticles of the apparatus with analyte molecules with during exposing 350 is a result of weak or strong binding interactions including, but not limited to, one or more of adsorption, physisorption, chemisorption and covalent bonding with the analyte molecules. For example and not by way of limitation, exposing 350 may involve an interaction between Au nanoparticles on the nanowire surface with an analyte molecule having a thiol-containing moiety. In another non-limitive example, exposing 350 may involve an interaction of Ag nanoparticles on the nanowire surface with an analyte molecule having a nitrogen-containing moiety.

A wide variety of analyte molecules may be sensed using the composite nanostructure apparatus in the method 300 of molecular sensing. For example, such analyte molecules to be sensed include, but are not limited to, organic molecules and inorganic molecules. In some embodiments, the analyte molecule may be one or more of a dye, a natural or synthetic biological molecule and an optically active chromophor. In other embodiments, the analyte molecule may be one or more of a toxin, a poison, and an explosive. In each example, the analyte molecule comprises a detectable feature to be sensed either optically or electrochemically.

Examples of dyes include, but are not limited to, a fluorescent xanthene derivative, such as Rhodamine 6G (R6G), fluorescein and texas red, which are used to label molecules for analysis, for example. Examples of a biological molecule include, but are not limited to, a nucleic acid, a protein, and any of their precursor molecules, such as nucleotide bases and amino acids, respectively, such that bacterial and viral analyte molecules may be sensed, for example.

Sensing 370 an analyte molecule bound to the metal nanoparticles of the array comprises using one or both of an optical mode of detection and an electrochemical mode of detection to sense 370 the bound analyte molecule. For example and not by way of limitation, a Raman-active analyte molecule is sensed 370 optically using one or both of Raman spectroscopy and surface-enhanced Raman spectroscopy (SERS). A redox-active analyte molecule is sensed 370 using an electrochemical technique including, but not limited to, one or both of voltammetry and amperometry. Moreover, the analyte molecule may comprise a bioactive moiety, such as an analyte protein or enzyme. Bioactive analyte molecules may be sensed 370 using a variety of spectroscopy techniques including, but not limited to, the optical and electrochemical techniques mentioned above.

The method 300 of molecular sensing using a composite nanostructure apparatus provides for analysis of minute quantities of an analyte molecule. Further, molecular sensing using such a composite nanostructure apparatus according to the method 300 provides areas of greater sensitivity than using a nanowire array without metalized nanowire surfaces (i.e., deposited metal nanoparticles). An example of an analyte molecule that was sensed 370, according to an embodiment of the method 300 of molecular sensing of the present invention, is further described herein in an 'Example' section. In some embodiments, the method 300 of molecular sensing is effectively a method of making nanostructures Raman active for one or more of Raman spectroscopic analysis and surface-enhanced Raman spectroscopic (SERS) analysis, for example and not by way of limitation.

Figure 4:
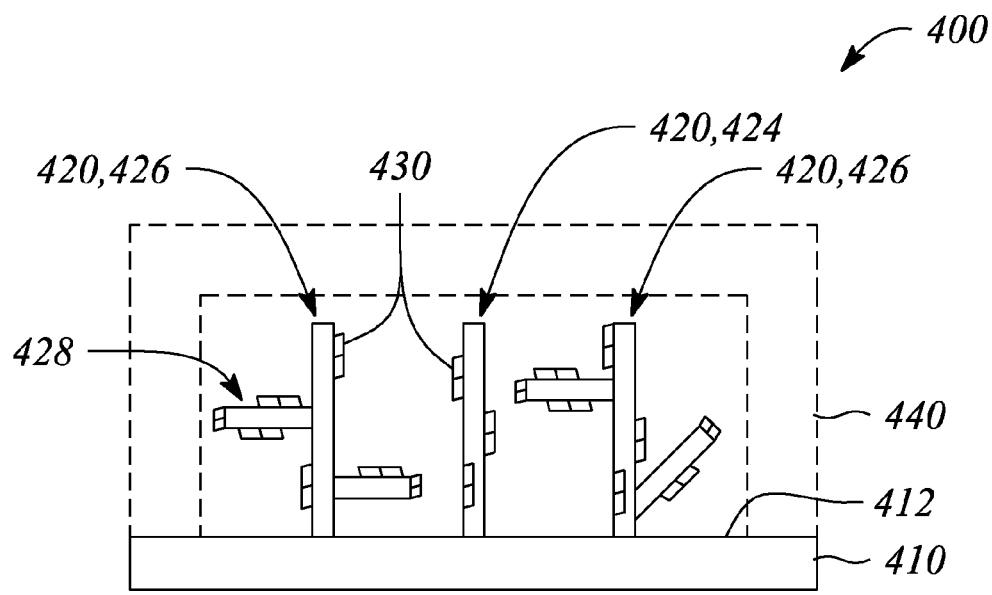
FIG. 4 illustrates a side view of a molecular sensor according to an embodiment of the present invention.

In another embodiment of the present invention, a molecular sensor is provided. FIG. 4 illustrates a side view of a molecular sensor 400 according to an embodiment of the present invention. The molecular sensor 400 is a discrete device with applications in a variety of different sensing environments. The molecular sensor 400 collects an analyte molecule or a number of different analyte molecules in the sensing environment. The collected analyte molecules are bound to nanowire-based collectors, as described further herein. The bound analyte molecules are detected or sensed using one or more of the optical and electrochemical techniques described herein.

The molecular sensor 400 comprises an array of nanowires 420 on a planar surface 412 of a substrate 410. In some embodiments, the array of nanowires 420 are grown from the planar surface 412 and extend from the surface 412 at any one or more angles to the plane of the substrate surface 412. FIG. 4 illustrates one embodiment where the angle is about 90 degrees to the planar surface 412 for simplicity of illustration only and not by way of limitation. The illustrated embodiment also provides a relatively unencumbered nanowire surface area. The nanowire array comprises one or both of primary or unbranched nanowires 424 and branched nanowires 426. The branched nanowires 426 comprise one or more nanowire branches 428, as illustrated in FIG. 4. A variety of branched and unbranched nanowires provides relatively greater sensing surface area to the molecular sensor 400 than unbranched nanowires 424 alone.

The molecular sensor 400 further comprises metal nanocrystals 430 deposited on at least some surfaces of the nanowires 420 in the array. The metal nanocrystals 430 on the nanowire surfaces may range from a metal nanoparticle to an accumulation of metal nanoparticles in various locations on the nanowire surfaces, including on branched surfaces when present. In some embodiments, the nanowire array 420 having deposited metal nanocrystals 430 is equivalent to the composite nanostructure apparatus 200, as described above. As such, the nanowire array 420 having deposited metal nanocrystals 430 will be referred to herein as 'the composite nanostructure apparatus' for simplicity of discussion herein and not by way of limitation. Further, in some embodiments, the composite nanostructure apparatus may be fabricated using one or both of the method 100 of making composite nanostructures and the method 300 of molecular sensing, both described above.

In some embodiments, the molecular sensor 400 further comprises a housing 440 that connects or supports the substrate 410 and surrounds at least a portion of the composite nanostructure apparatus. The housing 440 also provides sufficient exposure of the composite nanostructure apparatus to the environment. Moreover, the housing 440 may be attached to the planar substrate 410 in a variety of ways to provide temporary or permanent attachment, depending on the embodiment.

Figure 5:
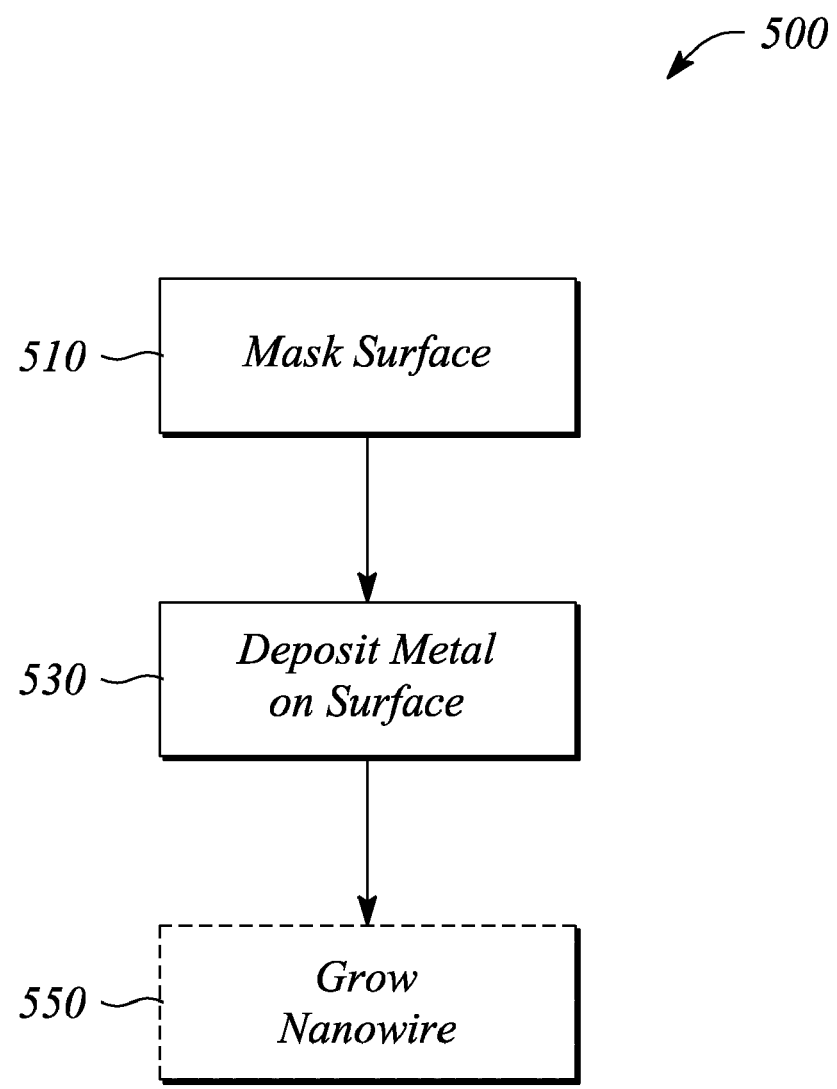
FIG. 5 illustrates a block diagram of a method of forming catalyzing nanoparticles on a selected location of a surface from which a nanowire grows according to an embodiment of the present invention.

In another embodiment of the present invention, a method of forming catalyzing nanoparticles in a selected location on a surface to direct or guide (i.e., control) nanowire growth is provided. FIG. 5 illustrates a block diagram of the method 500 of forming catalyzing nanoparticles in a selected location on a surface from which a nanowire will grow. The method 500 of forming catalyzing nanoparticles in a selected location comprises masking 510 a surface of a substrate, such that the selected location of the surface is exposed. In some embodiments, the surface may be a planar surface or a non-planar surface of a semiconductor wafer, for example, having any crystal lattice orientation. In other embodiments, the surface may be a surface of a nanostructure, such as a surface of a nanowire, which may be a planar surface or a non-planar surface. In some embodiments, the surface may comprise a level of doping, as is known in the art. For the purpose of simplicity of discussion herein and not by way of limitation, the method 500 of forming catalyzing nanoparticles on a selected location will be discussed with reference to the surface being a surface of a semiconductor substrate. A further description of forming catalyzing nanoparticles on a selected location of a surface of a nanostructure will be described with reference to an embodiment of a method 600 of forming a branched nanowire, as provided below.

The planar surface of a semiconductor substrate may be a horizontal plane, a vertical plane or any plane in between. Moreover, the planar surface of the semiconductor substrate may be accessed and exposed for the purposes of the method 500 by etching the substrate along internal crystal lattice planes of the semiconductor. For example and not by way of limitation, the semiconductor substrate may have a (110) horizontal planar surface or a (111) horizontal planar surface. Further, the exemplary (110) substrate may be etched along vertical (111) lattice planes to expose a vertical (111) planar surface. The non-planar surface of the semiconductor substrate may be achieved by etching the semiconductor substrate using known etching techniques to form non-planar surfaces.

In some embodiments, masking 510 a surface comprises forming a mask layer on the surface of the substrate to create a masked 510 surface that comprises a mask pattern that exposes the selected location. The mask layer includes, but is not limited to, oxides and nitrides of the substrate material. In some embodiments, an oxide layer is grown or deposited on the surface of the substrate, such as by using thermal oxidation in air (i.e., non-native oxide layer). In other embodiments, the oxide layer is a native oxide layer on the substrate surface, wherein the native oxide is intrinsically formed. In either embodiment, the coated substrate surface is the masked 510 surface.

In some embodiments, masking 510 a surface comprises forming a patterned etch mask with either a layer of a non-native oxide or nitride on a first surface of the substrate, and etching the first surface to expose a second surface of the substrate according to a pattern defined in the patterned etch mask. For example, a (110) substrate having a horizontal (110) surface (or the 'first surface') may be etched to expose a vertical (111) surface (or the 'second surface') according to this embodiment. In this embodiment, the second surface is further coated with either a non-native oxide or nitride layer, for example, and becomes the masked 510 surface to the exclusion of the first surface. Techniques for etching the mask layer and the substrate are known in the art.

In some embodiments, masking 510 a surface comprises forming a selected pattern on the masked 510 surface, such that the selected location is exposed. In some of these embodiments, forming a selected pattern on the masked 510 surface comprises patterning the masked 510 surface with an etch mask and removing the oxide or nitride mask material from a selected location (i.e., one or more selected locations) on the masked 510 surface to form a patterned masked surface. The selected location on the patterned masked surface is a predetermined location of an exposed surface (i.e., without non-native oxide or nitride) from which a nanowire may be subsequently grown. In some embodiments, the selected location is a discrete location on the patterned surface.

The method 500 of forming catalyzing nanoparticles in a selected location on a surface further comprises depositing 530 a metal nanoparticle on the selected location. Depositing 530 a metal nanoparticle comprises using electrochemical deposition. The metal is deposited 530 in the exposed selected location of the masked 510 surface, to the exclusion of other locations of the masked 510 surface using one of electrodeposition and electroless deposition. Depositing 530 using electroless deposition comprises exposing the masked 510 surface to a deposition solution of a metal salt. In some embodiments, the deposition solution comprises a metal salt and an enhancer, as defined above, such that deposition of the metal nanoparticle to the exposed selected location is promoted or enhanced, as described above.

In some embodiments, depositing 530 a metal nanoparticle on the selected location is equivalent to the electrochemical deposition 130 of the method 100 of making a composite nanostructure. For example, the enhancer facilitates metal deposition to a surface, as is further described above. In some embodiments, the enhancer is one of an oxide etchant and a chemical reductant. For example, the solution enhancer includes, but is not limited to, one or more of a fluoride solution, an aldehyde, a carbohydrate and hydrazine. In some embodiments, the enhancer removes any native oxide formed on the selected location after masking 510 a surface. In some embodiments, the enhancer controls or limits oxidation of the selected location. In other embodiments, the enhancer promotes metal deposition on the oxide-free surface of the selected location. Metal ions adjacent to or in contact with the selected location reductively deposit from the solution as metal nanoparticle(s) on the surface in a surface-mediated redox reaction, according to some embodiments.

For example, a deposition solution comprising an aqueous gold salt (e.g., $NaAuCl_4$) solution that does not include a fluoride solution enhancer will electrochemically deposit gold nanoparticles on a hydride-terminated silicon surface. However, the silicon surface is subject to oxidation by the water in the aqueous solution. Therefore, improved nanoparticle deposition on silicon is observed using a deposition solution comprising a nonaqueous gold salt (e.g., $NaAuCl_4$) solution and one or both of a chemical reductant as an enhancer and a hydride-terminated silicon surface. Electroless deposition of metal nanoparticles on silicon surfaces from non-aqueous solutions minimizes the oxidation of the silicon that can occur in an aqueous solution.

The other substrate surfaces, as well as locations on the masked 510 surface other than the selected locations, all of which are coated with the above-mentioned mask layer, do not participate in the surface-mediated redox reaction with the deposition solution of a metal salt. For example, the non-native oxide mask layer prevents or retards spontaneous reduction of a metal from solution on such non-native oxide coated surfaces. As such, the placement or deposition of the metal nanoparticle(s) on the masked 510 surface is controlled at least by using electrochemical deposition on the masked 510 surface of the method 500 of forming catalyzing nanoparticles.

As mentioned above for the method 100 of making a composite nanostructure, the deposited metal may be in the form of a nanoparticle of the metal or an accumulation of metal nanoparticles, depending on the embodiment. Therefore, in some embodiments, such as where the metal deposition 530 produced an accumulation of the metal nanoparticles (e.g., a continuous layer or film) on the selected location of the masked 510 surface, the method 500 of forming catalyzing nanoparticles further comprises annealing the deposited 530 metal into a nanoparticle catalyst on the selected location. The deposited metal is annealed using methods known in the art. In other embodiments, the method 500 of forming catalyzing nanoparticles may further comprise annealing to facilitate cleaning the surface and removing contamination. As such, the masked 510 surface having deposited 530 metal comprises nanoparticle catalysts on the selected location to the exclusion of all other surfaces, according to the method 500 of forming catalyzing nanoparticles.

In some embodiments, the method 500 of forming catalyzing nanoparticles further comprises growing 550 a nanowire from the selected location that comprises the metal nanoparticle. Growing 550 a nanowire comprises using any metal-catalyzed CVD growth processes mentioned above including, but not limited to, a metal-catalyzed VLS growth process, for example. Various nanowire growth techniques are known in the art.

In some embodiments, the method 500 of forming catalyzing nanoparticles on a selected location is particularly useful in reducing spurious nanowire growth and stray conducting paths on surfaces that can be detrimental to an end product. For example, nonselective metal deposition using a process such as angled vapor deposition to deposit the catalyst material will deposit nanoparticles onto both targeted surfaces (i.e., the selected locations) and untargeted surfaces (i.e., non-native oxide surfaces of the substrate). Moreover, using a process such as surfactant stabilized metal colloids might deposit nanoparticles on the untargeted surfaces, as well as the targeted surfaces, depending on the details of the deposition process. Deposition on such untargeted surfaces may lead to one or both of spurious nanowire growth and stray conducting paths during subsequent processing. Moreover, in some embodiments, the method 500 of forming catalyzing nanoparticles on a selected location reduces contamination of the metal catalyst particles by avoiding additional steps needed to immobilize pre-formed nanocrystals onto the surface. The catalyzed nanoparticles on the selected locations of the masked 510 surface provide controlled grow points or locations to guide or direct the subsequent nanowire growth 550 using a metal-catalyzed VLS growth process, for example.

Figure 6:
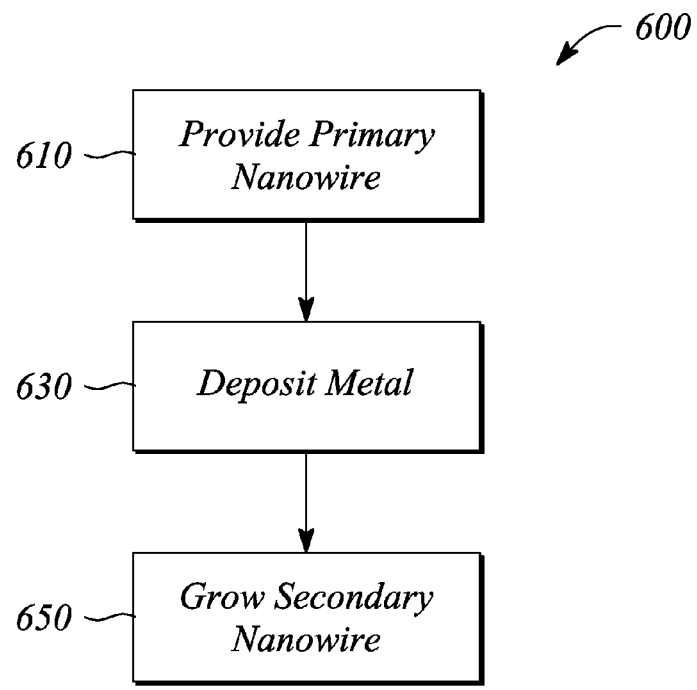
FIG. 6 illustrates a block diagram of a method of forming a branched nanowire according to an embodiment of the present invention.

In another embodiment of the present invention, a method 600 of forming a branched nanowire is provided. FIG. 6 illustrates a block diagram of the method 600 of forming a branched nanowire according to an embodiment of the present invention. The method 600 of forming comprises providing 610 a primary nanowire to a surface of a substrate. In some embodiments, a metal-catalyzed VLS growth technique is used to provide 610 the primary nanowire. In such embodiments, providing 610 comprises preparing the substrate surface with a nanoparticle catalyst in a location of the surface where the primary nanowire is to be provided 610; and introducing a gas comprising a precursor nanowire material to the substrate surface such that nanowire growth is initiated from the location on the surface of the nanoparticle catalyst. The primary nanowire grows from the substrate surface essentially linearly and at an angle to the substrate surface from the location of the nanoparticle catalyst. See, for example, the description above for nanowire growth and the above-cited U.S. patent applications for additional information on nanowire growth techniques. In other embodiments, the primary nanowire is provided 610 to the substrate surface using other techniques known in the art.

The primary nanowire is provided 610 at any angle to a surface plane of the substrate ranging from 0° to 180°. For example, FIG. 2 illustrates at least exemplary primary nanowires 224 that are provided 610 at an angle of about 90° from the surface plane 212 of the substrate 210 for the composite nanostructure apparatus 200 described above. The angle of the primary nanowires 220, 224 illustrated in FIG. 2 is about 90° therein for the purpose of simplicity of illustration and not by way of limitation. It should be understood that the primary nanowire may be provided 610 at any angle from the substrate surface in the above-mentioned range and still be within the scope of the method 600 of forming a branched nanowire.

In some embodiments, providing 610 a primary nanowire comprises depositing a nanoparticle catalyst using the above-described method 500 of forming catalyzing nanoparticles to provide 610 the primary nanowire in a selected location of the substrate, as described above. In other embodiments, depositing a nanoparticle catalyst uses other methods known in the art, such as physical vapor deposition, e-beam evaporation, thermal evaporation and sputtering, for example, and lithography techniques, to ultimately provide 610 the primary nanowire in a selected location of the substrate. In some embodiments, the substrate surface is a (111) surface of a semiconductor substrate. In those embodiments, the primary nanowire grows linearly and preferentially perpendicular to the (111) surface. In other embodiments, the semiconductor substrate has a different crystal lattice orientation.

The method 600 of forming a branched nanowire further comprises depositing 630 a metal nanoparticle on a surface of the primary nanowire using electrochemical deposition, as described above for the method 100 of making a composite nanostructure. Specifically, either electrodeposition or electroless deposition may be used for depositing 630. Using electroless deposition, metal nanocrystals are reductively deposited 630 from a metal salt in a deposition solution that further comprises an enhancer onto the surface of the primary nanowire. The metal nanocrystals are electrochemically deposited 630 on the primary nanowire surface to the exclusion of other surfaces, especially surfaces of the substrate having a non-native oxide layer or coating, similar to that described above for the method 500 of forming catalyzing nanoparticles. The metal nanocrystals deposited 630 on the primary nanowire range from a discrete nanoparticle of the metal (e.g., nanoparticle catalyst) to an accumulation of metal nanoparticles, which may be either a continuous or discontinuous film or layer, on the primary nanowire surface. The location of the deposited metal nanocrystals dictates the possible locations of nanowire branch formation on the primary nanowire.

The method 600 of forming a branched nanowire further comprises growing 650 a nanowire branch or secondary nanowire from a location of a metal nanoparticle on the primary nanowire. In some embodiments, growth 650 of the nanowire branch uses a metal-catalyzed VLS growth technique, referenced supra. As such, the nanowire branch is grown 650 on the primary nanowire from the location on the primary nanowire surface that the metal nanoparticle was deposited. In some embodiments, growing 650 a nanowire branch may comprise first annealing the deposited metal on the primary nanowire surface to form discrete metal nanoparticle catalysts. Annealing is described above with reference to the method 500 of forming catalyzing nanoparticles on a selected location. In other embodiments, a discrete metal nanoparticle is deposited 630 directly on the primary nanowire surface and therefore, annealing is optional, as described above. The nanowire branch may comprise either a material of the primary nanowire or another nanowire material, as described above, depending on whether the branched nanowire is intended to be homogeneous or heterogeneous. For example, the primary nanowire may be homogeneous along its axial length and include a nanowire branch that is made of a nanowire material different from the primary nanowire material. In this example, the branched nanowire 220, 226, 420, 426 is considered a heterogeneous nanowire.

Referring back to FIG. 2, exemplary branched nanowires 220, 226 are further illustrated in the composite nanostructure apparatus 200. As illustrated in FIG. 2, a nanowire branch 228 may grow 650 either perpendicular to the surface 222 of the primary nanowire 220 or at an angle other than 90° to the primary nanowire surface 222. FIG. 2 is illustrative only and not intended to limit the scope of possible profiles of branched nanowires 220, 226 that may be achieved according to the method 600 of forming a branched nanowire.

In some embodiments, the method 600 of forming a branched nanowire may be used to form branched nanowires in arrays, such as in the nanowire arrays described above with respect to the composite nanostructure apparatus 200 illustrated in FIG. 2, for example. Moreover, the method 600 of forming a branched nanowire may be used to form branched nanowires in arrays, such as the nanowire array described above with respect to the molecular sensor 400 illustrated in FIG. 4, in some embodiments.

In some embodiments, the method 600 of forming a branched nanowire further provides secondary nanowire branching. In these embodiments, the method 600 further comprises electrochemically depositing a metal from a solution comprising a metal salt and an enhancer onto surfaces of the grown 650 nanowire branches and growing a secondary nanowire branch from a previously grown 650 nanowire branch according to the method 600 of forming a branched nanowire, as described herein. In effect, depositing 630 and growing 650 are repeated, such that a target level of branching complexity may be achieved.

As a result, the branched nanowires comprise either primary nanowire branching (220, 226, 420, 426 in FIGS. 2 and 4) or both primary and secondary nanowire branching (illustrated in FIG. 2 as nanowire branch 229, by way of example and not limitation). One skilled in the art may expand the concept of nanowire branching, as described herein, and still be within the scope of the various embodiments of the present invention. The branched nanowires 220, 226, 229, 420, 426 used in nanowire arrays, such as those illustrated in FIGS. 2 and 4, provide increased effective surface area relative to the primary or unbranched nanowire 220, 224, 420, 424. Further, such branched nanowires facilitate or enhance the overall sensitivity of the nanowire array for one or both of optical sensing and electrical sensing.

As mentioned above for the method 500, a catalyzing nanoparticle can be formed on a selected location of a surface of a nanostructure, instead of on a semiconductor substrate, in some embodiments. With respect to the method 600 of forming a branched nanowire, the provided 610 primary nanowire is an example of a surface of a nanostructure on which the method 500 of forming catalyzing nanoparticles may be used according to some embodiments, as mentioned above. In some embodiments, the surface of the nanowire may have any shape and be oriented in any orientation relative to a substrate from which the nanowire is provided 610. Moreover, the nanowire may be provided 610 by any known method. In some embodiments, the nanowire is grown using a CVD growth process, as described above for the method 100 of making composite nanostructures. In some embodiments, a composition of the nanowire is homogeneous. In other embodiments, the composition of the nanowire is heterogeneous along its axial length, as described above for some embodiments of the composite nanostructure apparatus 200.

In some embodiments, the method 600 of forming a branched nanowire provides one or both of a selectable location of a nanowire branch and a controllable spacing of nanowire branches. In these embodiments, the provided 610 primary nanowire is heterogeneous. As such, according to these embodiments, providing 610 a primary nanowire comprises providing 610 a heterogeneous primary nanowire that has at least two adjacent axial segments of different nanowire materials. The different materials of adjacent axial segments facilitate selected nanowire branch locations. In some embodiments, the heterogeneous nanowire comprises nanowire segments of a first material alternating with nanowire segments of a second material, where the first material is different from the second material. The different materials include, but are not limited to, any of the nanowire materials listed above. In some embodiments, an axial length of one or more of the segments is controlled during primary nanowire growth to facilitate control of subsequent nanowire branch spacing.

FIG. 7 illustrates a side view of an exemplary branched nanowire 726 with one or both of selected nanowire branch locations and controlled nanowire branch spacing according to an embodiment of the present invention. The branched nanowire 726 comprises a heterogeneous primary nanowire 720 shown on a substrate 710 and one or more nanowire branches 728. FIG. 7 illustrates the heterogeneous primary nanowire 720 with five (5) nanowire segments, for example and not by way of limitation. The segments are numbered 1-5 in FIG. 7, wherein adjacent segments are made of different nanowire materials. For example and not by way of limitation, a Si—Ge heterojunctioned primary nanowire may have one or more axial alternating segments of silicon and germanium.

Providing 610 a primary nanowire further comprises forming an oxide layer on the surface of the heterogeneous primary nanowire 720. In some embodiments, forming an oxide layer may use the process described above for masking 510 a surface in the method 500 of forming catalyzing nanoparticles. As such, either a native oxide layer or non-native oxide layer is formed on the heterogeneous primary nanowire, depending on the embodiment. Referring back to the Si—Ge heterojunctioned nanowire example, as a result of forming an oxide layer, the Si segment has a $SiO_2$ layer while the Ge segment has a $GeO_2$ layer.

Providing 610 a primary nanowire further comprises selectively removing the oxide layer from a target axial segment of the primary nanowire 720 to the exclusion of other axial segments of the primary nanowire 720, such that the nanowire material of the target axial segment is exposed. In effect, the oxide layer is selectively removed from axial segments of a first material, but not from adjacent axial segments that comprise materials different from the first material. As such, a patterned oxide mask is effectively created or formed on the heterogeneous primary nanowire 720, as similarly described above some embodiments of masking 510 a surface of the method 500. The exposed axial segment facilitates locating a nanowire branch in a selected location, and in some embodiments facilitates controlled branch spacing when the axial length of the axial segments is controlled during growth.

Referring back to the Si—Ge heterojunctioned nanowire example, silicon dioxide is insoluble in water while germanium dioxide is soluble in water. Therefore, the oxide on a segment of either material may be removed to the exclusion of the other. For example and not by way of limitation, the oxide can be removed from the germanium segment using water as the solvent to the exclusion of the silicon segment. Referring back to FIG. 7, segments 1, 3 and 5 of the heterogeneous primary nanowire 720 have an oxide layer 722, for example and not by way of limitation a thermally grown non-native oxide layer, shown as shading on the respective segments, while segments 2 and 4 have the oxide layer removed to expose the nanowire material of these segments. The shading pattern essentially illustrates a patterned mask by way of example and not by way of limitation.

Once the oxide layer is removed from the axial segment of one of the different materials, a metal nanoparticle or nanocrystal is deposited 630 exclusively on the material of the exposed axial segment. In some embodiments, the deposition 630 is equivalent to depositing 530 a metal nanoparticle using electrochemical deposition according to some embodiments described above for the method 500 of forming a catalyzing nanoparticle. In some embodiments, the deposition 630 is equivalent to depositing 130 described above for the method 100 of making a composite nanostructure. In some embodiments, selectively removing the oxide layer from a segment is performed simultaneously with electrochemically depositing 130 a metal, as is described above for some embodiments of the method 100, for example.

As such, metal nanoparticles are deposited 630 on the surface of the exposed segments (i.e., selected segments), such as segments 2 and 4 in FIG. 7, to the exclusion of the unexposed (i.e., shaded) segments 1, 3 and 5. The deposited metal nanoparticles are essentially equivalent to the nanoparticle catalysts described above for the method 500 of forming catalyzing nanoparticles on a selected location.

Moreover, these embodiments of the method 600 of forming a branched nanowire with one or both of a selected nanowire branch location and a controlled nanowire branch spacing further comprise growing 650 a nanowire branch from the selected segments using the nanoparticle to catalyze the nanowire branch growth, as described above. FIG. 7 illustrates exemplary nanowire branches 728 from segments 2 and 4 of the heterogeneous primary nanowire 720, for example and not by way of limitation. The nanowire branches 728 may be made of the same material as the selected segment or another nanowire material may be used, such that the nanowire branches can be homogeneous or heterogeneous with respect to the segment from which the nanowire branch is grown 650.

According to these embodiments, the method 600 of forming branched nanowires can be used to fabricate one or both of the composite nanostructure apparatus 200 illustrated in FIG. 2 and the molecular sensor 400 illustrated FIG. 4. As such, the respective arrays of nanowires 220, 420 may comprise at least some branched nanowires 226, 426 that are heterogeneous 726, as in FIG. 7, and have one or both of selected nanowire branch locations and controlled nanowire branch spacing along the axial length of the heterogeneous primary nanowires 720, as illustrated in FIG. 7.

EXAMPLE

Anchored, p-type silicon nanowires with a typical diameter of about 25 nm were grown on a p-type (boron-doped) Si(111) wafer (resistivity ρ about 0.01-0.02 Ω-cm) using the gold-catalyzed CVD process described in Sharma, cited supra. The wafer was subsequently divided into smaller substrates, and each of the resulting substrates was cleaned in a mixture of $H_2SO_4:H_2O_2$ (1:1) for 5 min, rinsed with deionized water, and dried with $N_2$ gas.

To form a hydrogen-passivated surface on the nanowires, the resulting substrates were immersed in a 1% $HF/H_2O$ solution for approximately 3 minutes, rinsed for approximately 10-30 seconds, and dried under a stream of $N_2$. This dilute HF etch removed the native oxide layer and formed hydride terminations on the surface of the underlying silicon.

To investigate the deposition of solid metal deposits on the silicon nanowires, aqueous solutions of $AgNO_3$ (approximately 99.999% purity) and $NaAuCl_4 \cdot 2H_2O$ (approximately 99.9% purity) were prepared in a range of concentrations from approximately 1 mM to approximately 100 mM. The aqueous solutions were kept in the dark to prevent premature reduction of $Ag^+$ $^{and\ Au3+}$ in solution until the introduction of the hydrogen-passivated nanowires to deposit metal nanocrystals.

Three different techniques were used to apply the aqueous solutions of the metal salts to the hydrogen-passivated nanowires. In a first technique, immediately following the HF treatment to form the hydrogen-passivated nanowires, the silicon nanowire substrates were each spotted with an approximately 10 μL drop of one of the 1 mM solution of $AgNO_3$ or the 1 mM solution of $NaAuCl_4$ (i.e., first aqueous solution—without HF), which typically spread out to about a 5 mm diameter spot over the surface of the substrate.

In a second technique, in an effort to enhance the metal deposit coverage, about 2 μL of a 1% HF solution was added to the already dispensed approximately 10 μL drop of the respective 1 mM solution of either $AgNO_3$ or $NaAuCl_4$ (i.e., second aqueous solution—with added HF). The second aqueous solution was reacted with the hydrogen-passivated nanowire substrates using identical deposition parameters to those used in the first technique (i.e., first aqueous solution—without HF).

In a third technique, aqueous solutions of approximately 1% HF comprising approximately 1-100 mM of either $AgNO_3$ or $NaAuCl_4$ were prepared (i.e., third aqueous solution—with HF). The hydrogen-passivated substrate was immersed into the third aqueous solution for a predetermined duration (typically about 30 seconds) instead of applying drops of the aqueous solution onto the substrate, as described above for the first and second techniques. The immersed substrate was subsequently rinsed with purified water filtered to have a TOC (Total Organic Carbon)<about 3 ppb (>about 18 MΩ at pH about 5.5, determined by dissolved $CO_2$).

The immersion or third technique produced a larger surface area of metal deposition compared to the spotting of a drop in the first and second techniques. In particular, one or both of larger areas of metal deposits on the nanowires and improved spatial uniformity was observed. However, within the area where the nanocrystals were deposited, little or no differences in the quality or appearance of the metal deposits were observed between otherwise identical samples produced using either the second aqueous solution or the third aqueous solution, both with HF.

The nanowires were examined using an FEI model XL30 scanning electron microscope (SEM), typically operating at an accelerating voltage of 20 kV to examine morphological changes occurring on the nanowire surfaces with hydrogen-passivation and with subsequent solid metal deposition. Moreover, diluted solutions of R6G (an analyte molecule) were allowed to bind to the surfaces of the nanowires (e.g., both with and without solid metal deposits on the nanowire surfaces) and both Raman and XPS spectra were acquired. A Joriba-Yvon T64000 micro-Raman system equipped with a 100× plano-achromatic objective and a CCD detector were used for obtaining the Raman spectra. A standard X-ray photoelectron spectrometer equipped with an Al K α X-ray source (1486.6 eV) and a hemispherical analyzer was used for the XPS spectra.

A description of experiments performed and results obtained for the Example are also found in the above-cited article by A. A. Yasseri et al. "Growth and use of metal nanocrystal assemblies on high-density silicon nanowires formed by chemical vapor deposition", *Applied Physics A—Materials Science & Processing*, 82, 659-664 (2006), which is incorporated herein by reference in its entirety. The A. A. Yasseri et al. article includes exemplary spectra and micrographs of the results obtained for the Example. The A. A. Yasseri et al. article was published online Dec. 1, 2005© Springer-Verlag 2005.

Thus, there have been described various embodiments of a composite nanostructure apparatus and methods of making a composite nanostructure that one or both of may use selectively located catalyzing nanoparticles and may have branched nanowires, any combination of which may be used together for molecular sensing. It should be understood that the above-described embodiments are merely illustrative of some of the many specific embodiments that represent the principles of the present invention. Clearly, those skilled in the art can readily devise numerous other arrangements without departing from the scope of the present invention as defined by the following claims.

What is claimed is:

1. A method of making a composite nanostructure, the method comprising:
    masking a surface of a nanostructure;
    enhancing a deposition solution that comprises a metal salt; and
    electrochemically depositing a metal from the enhanced deposition solution onto the nanostructure,
    wherein enhancing a deposition solution comprises introducing an enhancer to the deposition solution, the enhancer promoting electrochemical deposition of the metal from the metal salt onto the nanostructure.

2. The method of making a composite nanostructure of claim 1, wherein electrochemically depositing a metal comprises using either electroless deposition or electrodeposition.

3. The method of making a composite nanostructure of claim 1, wherein the enhancer is selected from one or more of a fluoride solution, an aldehyde, a carbohydrate and hydrazine, the deposition solution being either an aqueous solution or a nonaqueous solution that depends on the selected enhancer.

4. The method of making a composite nanostructure of claim 1, wherein the enhancer is an oxide etchant selected from one or more of an aqueous hydrogen fluoride solution, an aqueous buffered hydrogen fluoride solution and a nonaqueous fluoride solution.

5. The method of making a composite nanostructure of claim 1, wherein the enhancer is a chemical reducing agent selected from one or more of an aldehyde, a carbohydrate and hydrazine, the deposition solution being a nonaqueous solution.

6. The method of making a composite nanostructure of claim 1, further comprising:
    forming a nanostructure prior to electrochemically depositing a metal, wherein forming a nanostructure comprises growing a nanowire having an axial length from a substrate using metal-catalyzed chemical vapor deposition growth.

7. The method of making a composite nanostructure of claim 1, wherein the enhancer one or both of controls oxidation of the nanostructure surface and causes metal nanocrystal formation on the nanostructure surface to promote electrochemical deposition of the metal.

8. The method of making a composite nanostructure of claim 7, wherein controlling oxidation and causing metal nanocrystal formation each comprises forming a hydrogen-passivated layer on the nanostructure surface, the hydrogen-passivated nanostructure surface acting as a reducing agent that reduces a metal ion from the metal salt to the metal nanocrystal.

9. The method of making a composite nanostructure of claim 1, further comprising:
    growing a nanowire from the nanostructure, the deposited metal on the nanostructure surface being a nanoparticle catalyst to facilitate nanowire growth, wherein the nanostructure is a primary nanowire, the grown nanowire being a secondary nanowire that branches from the surface of the primary nanowire.

10. The method of making a composite nanostructure of claim 1, wherein the nanostructure is an array of nanowires, the metal being a noble metal, and wherein the composite nanostructure is a molecular sensor, the deposited metal enhancing one or both of selectivity and sensitivity of the molecular sensor, such that an analyte molecule to be sensed preferentially interacts with the deposited metal on the nanowire array, and wherein the interacted analyte molecule is sensed using one or both an optical mode of detection and an electrochemical mode of detection.

11. The method of making a composite nanostructure of claim 1, wherein masking a surface of the nanostructure exposes a selected location of the surface through a mask layer, the metal being electrochemically deposited on the selected location.

12. The method of making a composite nanostructure of claim 10, wherein the deposited metal renders the nanowire array Raman-active for optically sensing the analyte molecule, the interacted analyte molecule being sensed using one or both of Raman spectroscopy and surface enhanced Raman spectroscopy (SERS), and wherein the electrochemical mode of detection comprises using one or both of voltammetry and amperometry.

13. A method of forming a catalyzing nanoparticle on a selected location of a surface from which a nanowire grows, the method comprising:

masking a surface of a nanowire, such that the selected location of the surface is exposed through a mask layer, the nanowire extending at a nonzero angle from a substrate; and electrochemically depositing a metal nanoparticle on the surface in the selected location from a deposition solution of a metal salt, such that the metal nanoparticle preferentially deposits on the surface of the selected location instead of on unexposed surfaces of the nanowire.

14. The method of forming of claim 13, wherein the mask layer is a non-native oxide layer, and wherein electrochemically depositing a metal nanoparticle comprises preferentially depositing the metal nanoparticle on an oxide-free surface of the selected location.

15. The method of forming of claim 13, further comprising growing a nanowire branch from the surface of the nanowire in the selected location using the deposited metal nanoparticle as a catalyst, such that a location of the grown nanowire branch on the surface is predetermined.

16. The method of forming of claim 13, wherein electrochemically depositing a metal nanoparticle comprises using electroless deposition of the metal nanoparticle, the deposition solution of a metal salt comprising an enhancer, such that the deposition of the metal nanoparticle in the selected location is enhanced relative to a deposition of the metal nanoparticle exclusive of the enhancer.

17. A method of forming a catalyzing nanoparticle on a selected location of a surface from which a nanowire grows, the method comprising:

masking a surface, such that the selected location of the surface is exposed through a mask layer; and electrochemically depositing a metal nanoparticle on the surface in the selected location from a deposition solution of a metal salt, such that the metal nanoparticle preferentially deposits on the surface of the selected location instead of on unexposed surfaces, wherein the surface is a surface of a heterogeneous nanowire having an axial length that comprises at least a first axial segment and a second axial segment adjacent to the first axial segment, at least one of the first and second axial segments has a controlled axial length, the axial segments comprising different nanowire materials, and wherein masking a surface comprises removing the mask layer from the first axial segment to expose the first axial segment to an exclusion of the second axial segment, and wherein electrochemically depositing a metal nanoparticle comprises preferentially depositing the metal nanoparticle on the exposed first axial segment to the exclusion of the second axial segment.

18. The method of forming of claim 17, further comprising growing a nanowire branch from the first axial segment using the metal nanoparticle as a catalyst, such that the grown nanowire branch has one or both of a selected nanowire branch location and a controlled nanowire branch spacing on the heterogeneous nanowire.

19. The method of forming of claim 17, wherein the deposition solution of a metal salt comprises an enhancer, such that the deposition of the metal nanoparticle in the selected location is enhanced relative to a deposition of the metal nanoparticle exclusive of the enhancer.

20. A method of making a composite nanostructure, the method comprising:

masking a surface of a nanostructure;

enhancing a deposition solution that comprises a metal salt; and electrochemically depositing a metal from the enhanced deposition solution onto the nanostructure, the nanostructure comprising a heterogeneous nanowire having an axial length that comprises at least a first axial segment and a second axial segment adjacent to the first axial segment, at least one of the first and second axial segments has a controlled axial length, the axial segments comprising different nanowire materials, a mask covering the second axial segment and exposing the first axial segment, wherein electrochemically depositing a metal comprises preferentially depositing the metal on the exposed first axial segment to the exclusion of the covered second axial segment, and wherein enhancing a deposition solution comprises introducing an enhancer to the deposition solution, the enhancer promoting electrochemical deposition of the metal from the metal salt onto the first axial segment.

* * * * *